US00PP23425P2

(12) United States Plant Patent
Werner et al.

(10) Patent No.: US PP23,425 P2
(45) Date of Patent: Feb. 26, 2013

(54) ***BUDDLEJA* PLANT NAMED 'MISS MOLLY'**

(50) Latin Name: ***Buddleja* hybrid**
Varietal Denomination: Miss Molly

(76) Inventors: Dennis James Werner, Raleigh, NC (US); Layne Karlton Snelling, Cary, NC (US)

( * ) Notice: Subject to any disclaimer, the term of this patent is extended or adjusted under 35 U.S.C. 154(b) by 101 days.

(21) Appl. No.: 12/931,039

(22) Filed: Jan. 24, 2011

(51) Int. Cl.
*A01H 5/00* (2006.01)

(52) U.S. Cl. ..... Plt./242
(58) Field of Classification Search ..... Plt./242
See application file for complete search history.

*Primary Examiner* — Kent L Bell

(57) ABSTRACT

*Buddleja* 'Miss Molly' is a new and distinct variety of butterfly bush that has the following unique combination of desirable features that are outstanding in a new variety.

1. Moderate vigor resulting in semi-compact growth habit.
2. Ease of asexual propagation using softwood or semi-hardwood cuttings.
3. Semi-upright growth habit with flowers borne stiffly on upright shoots.
4. Dark reddish-purple flower color, unknown in any other butterfly bush variety.

3 Drawing Sheets

Latin name of the genus and species: Genus: *Buddleja*. Species: hybrid.

Variety denomination: The inventive cultivar of *Buddleja* disclosed herein has been given the variety denomination 'Miss Molly'.

BACKGROUND OF THE INVENTION

The present invention relates to a new and distinct variety of *Buddleja* (butterfly bush) grown as an ornamental shrub for home and commercial landscapes. Butterfly bush is typically grown for its attractive, fragrant flowers that are borne throughout the growing season.

The new and distinct variety of butterfly bush resulted from a formal breeding program established by the inventors in Raleigh, N.C., United States. One of the objectives of the breeding program was to develop a semi-compact *Buddleja* with dark pink to near red flower color. 'Miss Molly' originated as a first generation descendant from a hand pollinated cross of *Buddleja* 'Attraction'×*Buddleja* 'Miss Ruby' made in 2004. 'Miss Ruby' (U.S. Plant Pat. No. 19,950) was developed by the present inventors, and is a first generation descendent of 'White Ball' butterfly bush (non-patented)×*Buddleja* 'Attraction' butterfly bush (non-patented). 'White Ball' was released and named as a butterfly bush cultivar in Booskoop, The Netherlands, in 1974, and is available in commerce. 'Attraction' was released in 2001. Both 'Miss Ruby', 'Attraction' and 'White Ball' are complex hybrids comprised of multiple species of *Buddleja*, and hence assigning a specific species designation to any of these cultivars is inappropriate.

The seeds resulting from the 2004 controlled hybridization process were harvested in fall of 2004 and germinated in a greenhouse in Raleigh, N.C. in the winter of 2005. The resulting 167 progeny were planted in field trials in spring of 2005. These plants flowered in summer 2005, and one seedling, designated NC2005-8, was selected for its semi-compact growth habit, attractive green leaf color, and attractive dark reddish-purple color. This original plant demonstrated characteristics identical to those subsequently expressed on other plants when propagated from stem cuttings. This single plant is the subject of the present invention 'Miss Molly'.

The distinguishing traits of 'Miss Molly' are semi-compact growth habit, green leaf color, and flowers that are dark reddish-purple in color. The flower color of 'Miss Molly' is unique in currently available butterfly bush. The cultural requirements for 'Miss Molly' are well-drained soil, full sun, and moderate moisture. 'Miss Molly' exhibits no serious pest or disease problems known to the inventors, except for occasional spider mite infestation during periods of hot, dry weather.

The closest comparison known to the inventors are the parents 'Miss Ruby' and 'Attraction'. Plants and flowers of this new variety differ from its parents. 'Miss Molly' produces a plant that is similar to the 'Miss Ruby' parent in size and stature, but possesses dark reddish-purple (RHS 61B) rather than the medium pink flowers of 'Miss Ruby' (RHS 71C). 'Miss Molly' is different than the 'Attraction' parent in being more compact in growth, and having dark reddish-purple flower color, as compared to the typical purple of 'Attraction' (RHS 77A).

The first asexual propagation of 'Miss Molly' was conducted by the inventors in fall 2005 in Raleigh, N.C., and 'Miss Molly' has subsequently been propagated in the same location in years 2006 and 2007. In all cases, the original plant selection was propagated asexually by softwood to semi-hardwood stem cuttings. Such cuttings root readily under mist in about 14 to 21 days, and resume normal growth. Ten plants derived from stem cuttings of the variety were established in test plots at Jackson Springs, N.C. in 2007, and three additional plants derived from stem cuttings of the variety were established at Raleigh, N.C. in 2006. During all asexual propagation, the characteristics of the original plant have been maintained. Plants derived from stem cuttings exhibit characteristics identical to those of the original plant, and no aberrant phenotypes have appeared.

Test plantings and performance evaluation over four years at Jackson Springs, N.C. and three years at Raleigh, N.C. demonstrate this variety to be relatively consistent in its characteristics even under the different growing conditions associated with yearly climatic variation.

Plants of the new variety are moderately vigorous after establishment in the field, being less vigorous and more compact than many cultivars of butterfly bush. Young plants have averaged about 0.6 meters of growth per year over the first two years of growth. Plants are semi-upright in growth habit, with dense branching. Flowering occurs in the first year of growth on newly formed wood. The inflorescence is a simple panicle, and shows a unique dark reddish-purple flower color. Flowering usually begins in late May to early June in Jackson Springs, N.C., and continues throughout the growing season until the first freeze event in October or November. An individual inflorescence flowers for about 7-10 days, depending on temperature, but new flowers are made during the entire growing season.

'Miss Molly' is distinguished from other related known cultivars based on the unique combination of traits including semi-compact growth habit, green leaf color, and dark reddish-purple flower color.

The new variety has been named the 'MISS MOLLY' cultivar. First public offer for sale of 'Miss Molly' was made in Grand Haven, Mich., U.S.A. on Aug. 1, 2010, but no sale of plants has yet taken place at the time of application.

SUMMARY OF THE INVENTION

'Miss Molly' is a new and distinct variety of butterfly bush that has the following unique combination of desirable features outstanding in a new variety. In combination these traits set 'Miss Molly' apart from all other existing varieties of butterfly bush known to the inventors.

1. 'MISS MOLLY' has moderate vigor resulting in semi-compact growth habit.
2. 'MISS MOLLY' is asexually propagated using softwood or semi-hardwood cuttings.
3. 'MISS MOLLY' demonstrates semi-upright growth habit with flowers borne stiffly on upright shoots.
4. 'MISS MOLLY' exhibits dense branching.
5. 'MISS MOLLY' has dark reddish-purple flower color, unknown in any other existing butterfly bush variety.

BRIEF DESCRIPTION OF THE DRAWINGS

The photographs in the drawings were made using digital photography techniques, and show the colors as true as reasonably possible by digital photography. Colors in the photographs may differ slightly from the color values cited in the detailed botanical description, which accurately describe the colors of the new *Buddleja* variety 'MISS MOLLY'. All photographs were taken from two-year-old plants growing at Jackson Springs, N.C.

DETAILED BOTANICAL DESCRIPTION OF THE VARIETY

Figure 1:
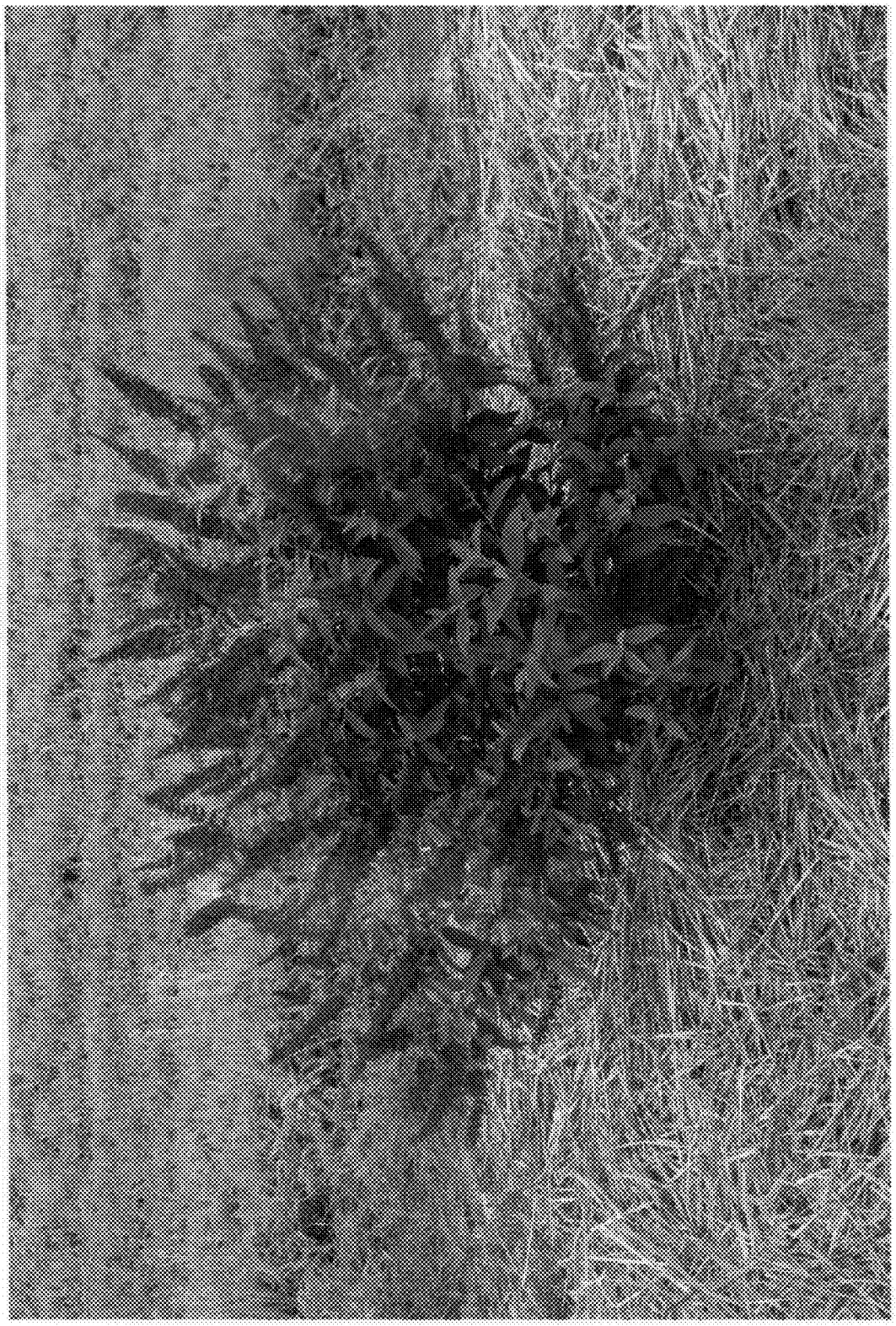
FIG. 1 shows a typical plant of 'MISS MOLLY', showing the semi-compact growth, upright habit, and unique dark reddish-purple flowers.
Figure 2:
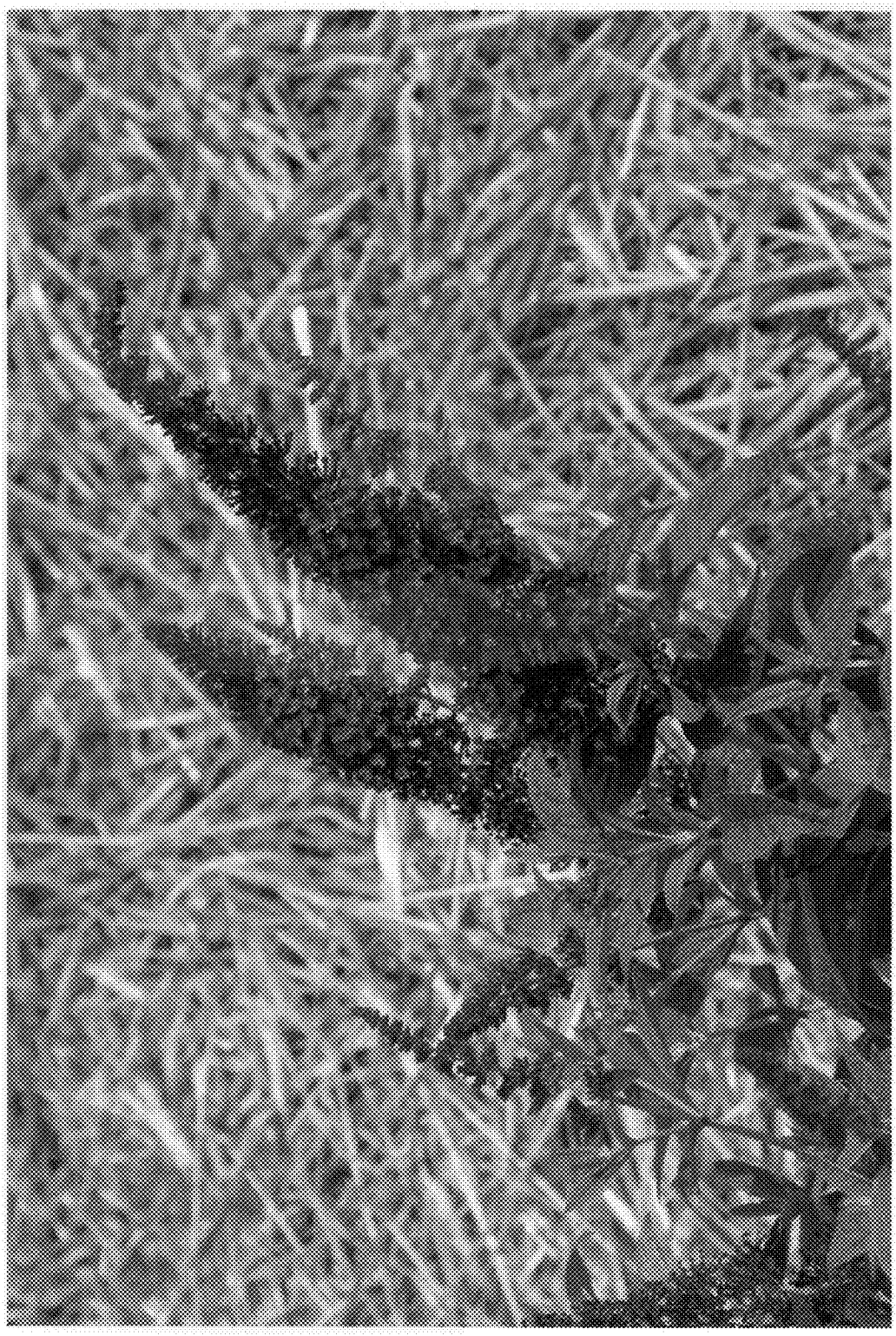
FIG. 2 shows a close-up view of the inflorescence of 'MISS MOLLY', showing the unique dark reddish-purple color of the individual flowers in the inflorescence.
Figure 3:
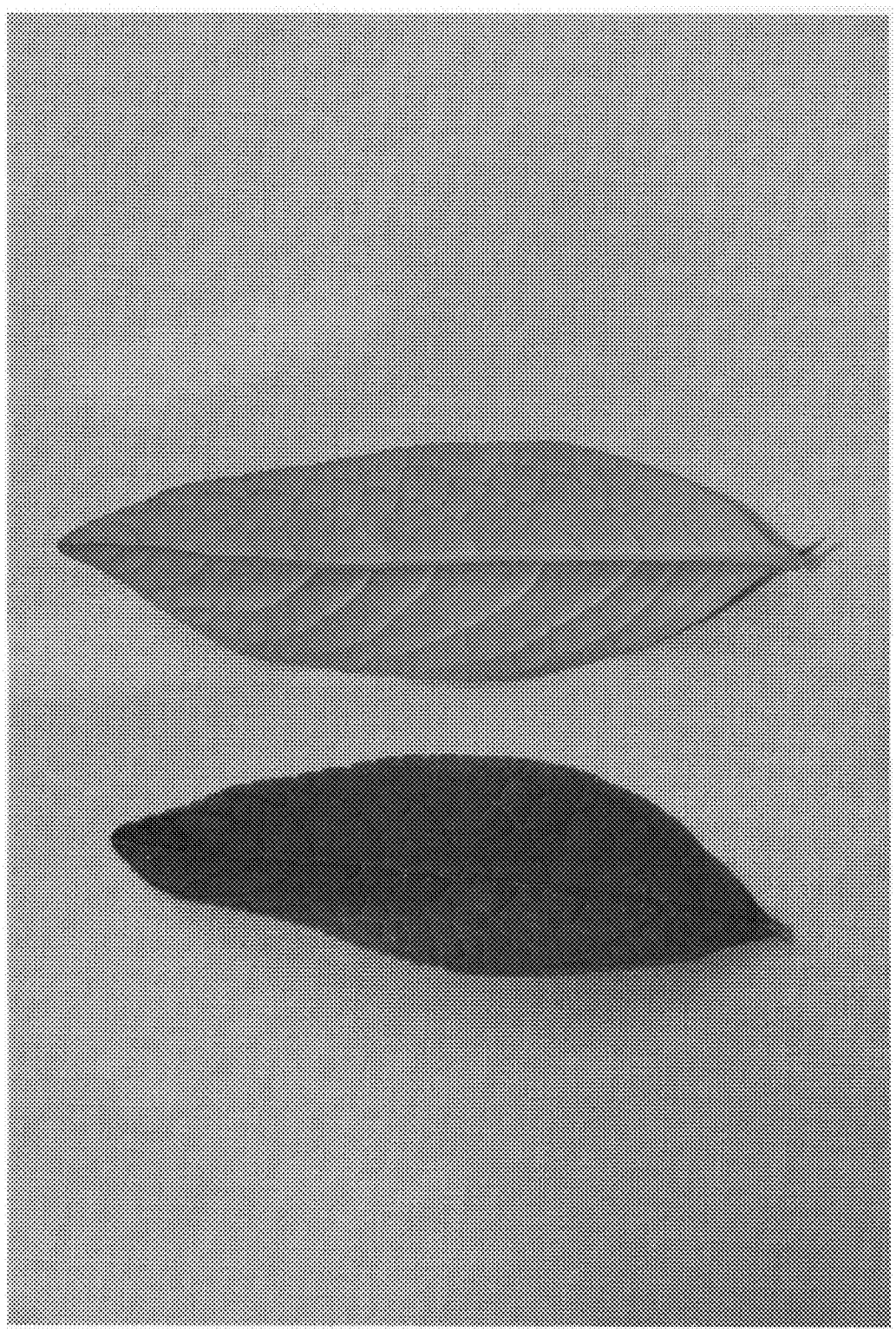
FIG. 3 shows the typical coloration and form of leaves of 'MISS MOLLY'. This figure shows the lower and upper leaf surface.

The following is a detailed description of the botanical and ornamental characteristics of the subject butterfly bush 'MISS MOLLY'. Color data are based on The Royal Horticultural Society Colour Chart, The Royal Horticultural Society, London, 2001 edition. Where dimensions, sizes, colors and other characteristics are given, it is to be understood that such characteristics are approximations of averages set forth as accurately as practicable.

The descriptions reported herein are from three-year-old specimens grown out-of-doors in Jackson Springs, N.C.

Genus: *Buddleja.*

Species: hybrid.

Denomination: 'MISS MOLLY'.

Commercial classification: Shrub, deciduous.

Common name: Butterfly bush.

Type: Ornamental.

Uses: Patio container plant, herbaceous perennial border, or shrub border for residential and commercial landscapes.

Cultural requirements: Full sun exposure, well-drained soil, and moderate moisture.

Parentage: 'MISS MOLLY' is a hybrid that resulted from the cross pollination of the following *Buddleja* parents: Seed parent='Attraction'. Pollen parent='Miss Ruby'.

Plant description:

*Blooming period.*—Spring, summer, and early fall until frost.

*Blooming habit.*—Upright with narrow inflorescences.

*Vigor.*—Moderate vigor.

*Plant habit.*—Semi-compact, dense, semi-upright habit.

*Height and spread.*—0.83 meters (height) and 1.4 meters (width). Three-year-old plants.

*Hardiness.*—To date, hardy to minus 8 degrees Centigrade. Not tested below this temperature. Adapted from USDA hardiness zones 6-9.

*Propagation.*—Softwood to semi-hardwood cuttings under intermittent mist. Roots typically form in 2-3 weeks.

*Root system.*—Fibrous.

*Seasonal interest.*—Dark reddish-purple flowers in spring, summer, and fall on a compact shrub.

*Disease and pest susceptibility and resistance.*—No particular susceptibility or resistance, except occasionally susceptible to spider mites under hot and dry conditions.

*Special growing requirements.*—Moderate yearly pruning in late winter or early spring prior to bud break is recommended to encourage more profuse flowering.

Stems:

*Shape.*—Stem cross section is quadrangular.

*Length.*—Average 53 cm in one year of growth.

*Color.*—Yellow-green (RHS 144C) on recently formed shoots.

*Diameter.*—3 mm near mid-portion of stem on current season growth.

*Stem surface.*—Glaucous.

*Pubescence.*—Absent.

*Internode length.*—4.0 cm. between nodes.

Foliage:

*Type.*—Deciduous.

*Leaf arrangement.*—Opposite, decussate.

*Leaf division.*—Simple.

*Leaf shape.*—Elliptic.

*Leaf base.*—Attenuate.

*Leaf apex.*—Acuminate.

*Leaf venation.*—Pinnate.

*Midvein color.*—Green (RHS 143D).

*Leaf surface*.—Glaucous (adaxial surface). Slightly pubescent (abaxial surface).
*Leaf margin*.—Serrulate.
*Leaf attachment*.—Petiolate.
*Petiole dimensions*.—3.4 mm length. 1.2 mm width.
*Petiole shape*.—Sulcate.
*Petiole color*.—Yellow-green (RHS 145D).
*Leaf color*.—Adaxial side=green (RHS 137A). Abaxial side=grayed-green (RHS 194B).
*Leaf length*.—Average length (10 leaves)=6.7 cm.
*Leaf width*.—Average width (10 leaves)=1.8 cm.
*Foliar fragrance*.—None detectable.

Flowers:
*Inflorescence*.—Terminal panicle.
*Petals*.—4 in number.
*Fused or unfused*.—Fused at base.
*Petal margin*.—Entire.
*Petal apex*.—Rounded lobes, serrulate.
*Petal base*.—Truncate.
*Petal surfaces*.—Glaucous.
*Petal shape*.—Rotund.
*Petal dimensions*.—8 mm. length. 3.0 mm. width.
*Petal color*.—Adaxial and abaxial surface=red-purple (RHS 61B).
*Flower shape*.—Salverform.
*Corolla tube color*.—Inside surface=yellow-orange (RHS 25A). Outside surface=red-purple (RHS 60C).
*Corolla tube surfaces* (*inner and outer surfaces*).—Pubescent.
*Corolla tube shape*.—Tubular.
*Color of peduncle*.—Grayed-green (RHS 194C).
*Peduncle surface*.—Glaucous.
*Peduncle shape*.—Flattened oval in cross section.
*Peduncle size*.—2 mm. length. <1 mm. diameter.
*Pedicel dimensions*.—1.0 mm. in length and less than 1 mm. in diameter.
*Pedicel color*.—Grayed-green (RHS 194C).
*Pedicel shape*.—Flattened oval in cross section.
*Pedicel surface*.—Glaucous.
*Flowers persistent or self-cleaning*.—Flowers are persistent.
*Lastingness of the overall inflorescence*.—2-3 weeks.
*Lastingness of an individual flower*.—3-5 days.
*Dimensions of inflorescence*.—10.6 cm in length. 3.0 cm in diameter at base, tapering to 1.6 cm at terminus.
*Dimensions of entire individual flower*.—8 mm. length. Diameter 7 mm at apex tapering to 1 mm at base.
*Quantity of flowers*.—Variable. Average of 150 flowers per individual inflorescence.
*Bud color*.—Red-purple (RHS 60A).
*Bud apex*.—Rounded.
*Bud surface*.—Glabrous.
*Bud shape*.—Elongated, linear balloon.
*Calyx shape*.—Tubular.
*Calyx dimensions*.—1.1 mm. in width and 2.7 mm. in length.
*Sepals*.—Four in number.
*Sepal shape*.—Lanceolate.
*Sepal apex*.—Acute.
*Sepal margin*.—Entire.
*Sepal surface*.—Glabrous.
*Sepal color*.—Outside surface, grayed-green (RHS 191B).
*Flower fragrance*.—Distinct sweet fragrance.

Reproductive organs:
*Stamens*.—Four, fused to inside of petals.
*Anther shape*.—Oblong.
*Anther color*.—White (RHS NN155A).
*Anther dimensions*.—1.0 mm in length and 0.2 mm wide.
*Filament size*.—No distinct filament. Anthers fused to corolla tube.
*Pollen amount*.—Moderate.
*Pollen color*.—Yellow-white (RHS 158D).
*Pistil*.—One in number.
*Pistil dimensions*.—4 mm. in length, and less than 1 mm. in diameter.
*Stigma color*.—Yellow-green (RHS 144A).
*Style shape*.—Cylindrical.
*Style color*.—Yellow-green (RHS N144D).
*Style length*.—3 mm.
*Ovary*.—Present.
*Ovary position*.—Superior.
*Ovary shape*.—Oval.
*Ovary color*.—Yellow-green (RHS144C).
*Fertility*.—Self-unfruitful. Requires cross pollination.

Fruit:
*Type*.—Swelled capsule.
*Dimensions*.—7.5 mm in length (variable) and 1.5 mm in diameter (variable).
*Color*.—Yellow-green (RHS 144C) when immature.

Herbarium voucher: A voucher of 'Miss Molly' will be deposited into the Herbarium of North Carolina State University (NCSU) in Raleigh, N.C., USA upon patenting.

That which is claimed is:

1. A new and distinct variety of *Buddleja* plant substantially as illustrated and described, characterized by its compact growth habit, green leaf color, and dark reddish-purple flower color.

* * * * *